(12) United States Patent
Maki (10) Patent No.: US 8,590,392 B2
(45) Date of Patent: Nov. 26, 2013

(54) COMPRESSION TEST SYSTEMS AND METHODS

(75) Inventor: Craig V. Maki, Virginia, MN (US)

(73) Assignee: Cliffs Natural Resources Inc., Cleveland, OH (US)

( * ) Notice: Subject to any disclaimer, the term of this patent is extended or adjusted under 35 U.S.C. 154(b) by 587 days.

(21) Appl. No.: 12/881,766

(22) Filed: Sep. 14, 2010

(65) Prior Publication Data

US 2012/0060581 A1 Mar. 15, 2012

(51) Int. Cl.
- *G01N 3/08* (2006.01)
- *G01D 7/02* (2006.01)
- *G01N 3/32* (2006.01)

(52) U.S. Cl.
USPC .................................. 73/818; 73/790; 73/813

(58) Field of Classification Search
None
See application file for complete search history.

(56) References Cited

U.S. PATENT DOCUMENTS

| | | | | |
|---|---|---|---|---|
| 3,610,034 A * | 10/1971 | Gunn, et al. | | 73/817 |
| 5,063,785 A | 11/1991 | Labuz et al. | | |
| 5,877,428 A * | 3/1999 | Scolton | | 73/822 |
| 6,279,388 B1 * | 8/2001 | Tsujii et al. | | 73/82 |
| 6,460,399 B1 * | 10/2002 | Beekman et al. | | 73/12.09 |
| 6,837,115 B2 | 1/2005 | Mansky | | |
| 2002/0170361 A1 * | 11/2002 | Vilendrer et al. | | 73/849 |
| 2003/0226404 A1 * | 12/2003 | Ouellet et al. | | 73/849 |
| 2008/0184807 A1 | 8/2008 | Nakano | | |

* cited by examiner

*Primary Examiner* — Andre Allen
(74) *Attorney, Agent, or Firm* — Hahn, Loeser & Parks LLP; Rex W. Miller, II (57) ABSTRACT

A system and method for determining the compressive strength of pellets are presently disclosed. A system includes a moveable feed tray adapted to support a plurality of pellets to be tested, a platen below the moveable feed tray and opposite a ram capable of applying compressive force to a pellet, a drive motor engaging the moveable feed tray, and a compressive force monitoring system including a force sensor. A method includes providing a feed tray and positioning a ram at a first position above a platen, advancing the feed tray to position a pellet at a test position between the ram and the platen, detecting the non-arrival of the pellet at the test position, retracting the ram from the first position, advancing the feed tray and operating the ram to determine the compressive strength of the pellet. Also disclosed is a calibration method for a compression test system.

20 Claims, 6 Drawing Sheets

COMPRESSION TEST SYSTEMS AND METHODS

BACKGROUND AND SUMMARY OF THE DISCLOSURE

The present disclosure relates to a system and method for determining the compressive strength of materials. Compression test systems have been commonly used to characterize or measure the compressive strength of materials, including mined materials such as taconite, agglomerated products, and other materials commonly provided in a pelletized form. The compressive strength of such pellets is important to ensure the pellets have sufficient strength to withstand transportation or other process operations. For example, during transportation substantial quantities of material may be placed into the hold of a ship or into containers for rail or truck transportation and, as the amount of material increases, substantial compressive force is applied to the pellets. Various systems have been developed to characterize the compressive strength or crushing strength of pellets, and requirements such as ISO 4700 have been developed to standardize these measurements.

Prior compression test systems have typically had limited throughput due to the time required to test a pellet. Test specifications or standards often impose a limit on the operating speed of the compressive test system, and in some cases, the operating speed has been limited to 10 to 20 millimeters per minute. To accommodate variation in pellet size, many prior test systems positioned the ram at a starting location sufficiently removed from the platen to accommodate the largest pellet expected to be tested. As most pellets have a diameter less than the diameter of the largest pellet to be tested, this prior approach to positioning the ram has resulted in increased test times as the ram is required to travel a greater distance for each pellet.

Additionally, prior test systems were often unable to accurately capture the maximum compressive strength of a pellet under test due to limitations of the test system. Substantial user intervention has often been required limiting the efficiency and throughput of prior compression test systems. To improve accuracy, the measurement device of prior test systems have often been tested by stacking known weights on the test system and verifying the accuracy of the measurement. The operating range of compression test systems often extends to several hundred pounds, and in some cases, to over 1,000 pounds. As a consequence, positioning this amount of weight on the test system has been cumbersome and has lead to complicated maintenance and calibration procedures for prior test systems.

In view of the limitations of prior systems, there remains a need for a system and method for determining the compressive strength of pellets that provide for increased efficiency and reduced costs. There also remains a need for a compression test system requiring less user intervention and allowing the testing of larger samples of pelletized materials. There also remains a need for a simplified maintenance and calibration system and method to improve the usability and maintainability of the compression test system.

Presently disclosed is a system for determining the compressive strength of pellets comprising a moveable feed tray adapted to support a plurality of pellets to be tested, a platen positioned below the moveable feed tray and opposite a ram capable of applying a compressive force to a pellet on the platen, a drive motor engaging the feed tray to position a pellet between the platen and the ram to permit compression testing of the pellet, and a compressive force monitoring system including a force sensor, where the compressive force monitoring system is capable of providing a first signal corresponding to the force applied by the ram to a pellet on the platen and capable of determining the maximum compressive force applied by the ram to the pellet on the platen.

In the system for determining the compressive strength of pellets, the ram may be hydraulically powered, and the moveable feed tray may be a rotating feed wheel. The feed wheel may include a plurality of apertures spaced along the circumference of the feed wheel, each aperture being adapted to support a pellet. In one embodiment, the feed wheel may have 100 or more apertures. The force sensor may comprise a load cell. The compressive force monitoring system may include a signal processor capable of determining the maximum compressive force applied to the pellet on the platen. A signal processor may determine the maximum compressive force applied to the pellet on the platen by analog peak capture. The moveable feed tray may further comprise a position indicator, and the position indicator may have a plurality of position indicating apertures, each position indicating aperture corresponding to a pellet support aperture of the feed tray.

The system for determining the compressive strength of pellets may further comprise a position detection system configured to detect the position of the feed tray, the position detection system having a light source on one side of the feed tray position indicator and an optical sensor opposite the light source on the other side of the feed tray position indicator, where the optical sensor receives light from the light sensor passing through a position indicating aperture when the feed tray is in a desired position.

Also disclosed is a method for determining the compressive strength of pellets that comprises providing a feed tray adapted to support a plurality of pellets to be tested, positioning a ram at a first position above a platen to apply a compressive force to a pellet on the platen, advancing the feed tray to position a pellet at a test position between the ram and the platen, detecting the non-arrival of the pellet at the test position, retracting the ram from the first position, advancing the feed tray to position the pellet beneath the ram, and operating the ram to determine the compressive strength of the pellet.

The step of detecting the non-arrival of a pellet may further comprise starting the advance of the feed tray and measuring the time the feed tray has been advancing to position a pellet at the test position between the ram and the platen, and identifying the non-arrival of the pellet at the test position when the measured time exceeds a predetermined time. The step of advancing the feed tray may further comprise advancing the feed tray to position a pellet at a test position between the ram and the platen until the ram in the first position interferes with an advancing pellet supported by the feed tray impeding the advance of the feed tray. The step of retracting the ram from the first position may comprise retracting the ram from the first position such that the ram does not interfere with the advancing pellet supported by the feed tray.

A method for determining the compressive strength of pellets may further comprise retracting the ram from the first position by a predetermined distance, advancing the feed tray to position the advancing pellet at the test position, detecting the non-arrival of the pellet at the test position, and repeating until the ram is sufficiently retracted from the first position such that the ram does not interfere with the pellet supported by the feed tray.

A method of calibrating a compression test system is also disclosed that comprises providing a compression test system having a platen engaging a first load cell and a ram opposite the platen, removing the platen of the compression test system, providing a second load cell with a known measurement accuracy above the first load cell, providing a calibration load applicator and a thrust bearing between the second load cell and the ram, the calibration load applicator being extendable to apply a calibration load to the compression test system, and calibrating the first load cell by comparing the force measured by the second load cell with the force measured by the first load cell. The calibration load applicator may be a threaded connector, such as a bolt or a modified platen.

A calibration system for calibrating a load cell of a compression test system is also disclosed, where the calibration system comprises a master load cell positioned above the load cell of the compression test system, and a calibration load applicator and a thrust bearing positioned between the master load cell and a ram of the compression test system, where the calibration load applicator is extendable to apply a calibration load to the compression test system.

BRIEF DESCRIPTION OF THE DRAWINGS

Reference is made to the accompanying drawings in which particular embodiments and further benefits of the invention are illustrated as described in more detail in the description below, in which.

DETAILED DESCRIPTION OF THE DRAWINGS

Figure 1:
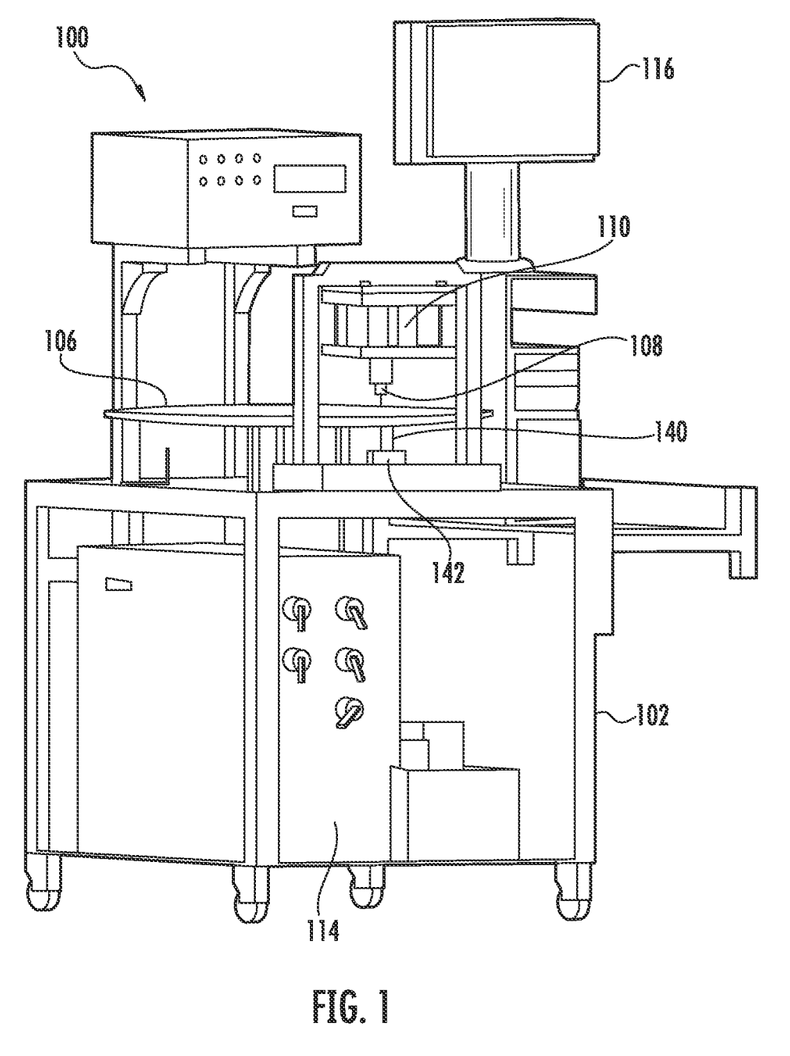
FIG. 1 is a perspective view of a compression test system of the present disclosure.
Figure 2:
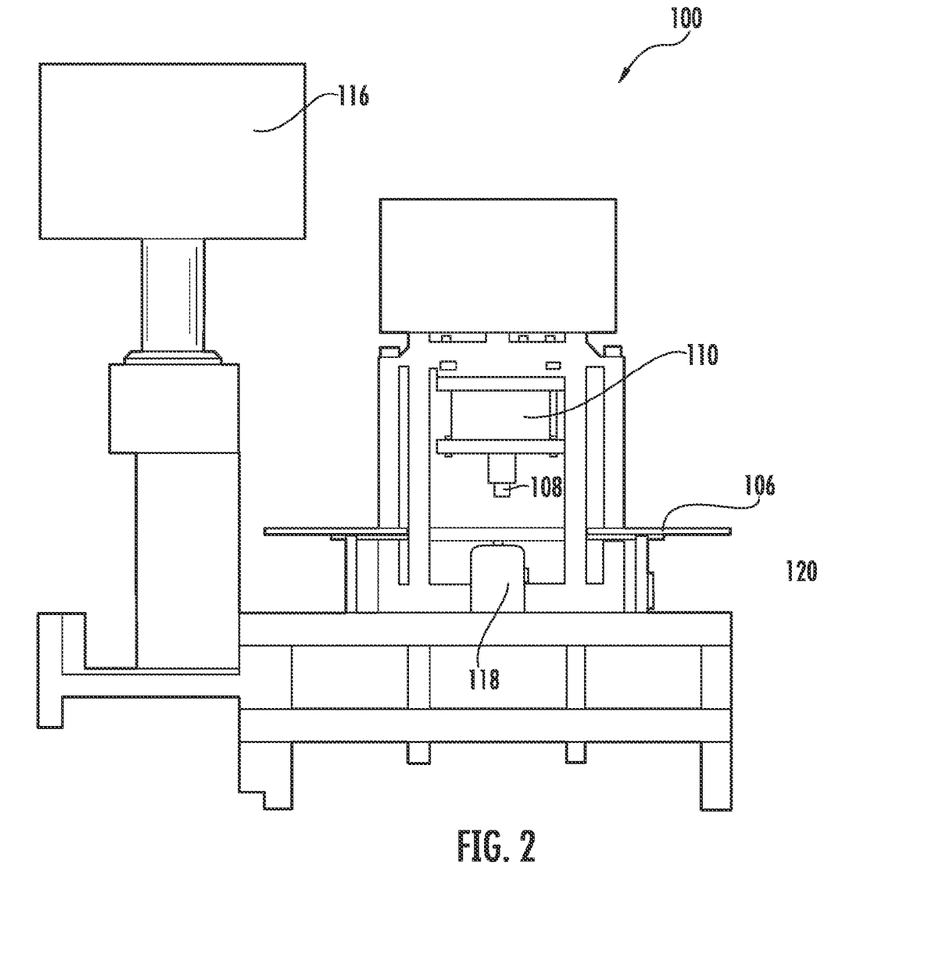
FIG. 2 is a side elevation view of a compression test system of the present disclosure.

Referring generally to FIGS. 1 through 7, a system for determining the compressive strength of pellets is disclosed. The system may be adapted to determine the compressive strength of various materials, including mined materials such as taconite, agglomerated products, or other pelletized materials. The system may be adapted for a wide range of pellet sizes, including pellets having a diameter of between 5 and 20 millimeters, and may be capable of measuring compressive strengths of up to 2,000 pounds or more. As illustrated in FIGS. 1 and 2, the compression test system 100 includes a moveable feed tray, such as a feed wheel 106, adapted to support a plurality of pellets to be tested. The system 100 also includes a platen 140 positioned opposite a ram 108, where the ram 108 is capable of applying a compressive force to a pellet on the platen 140. The system 100 also includes a drive motor 118 engaging the feed tray capable of moving the feed try to position a pellet between the platen and the ram to permit the compression testing of the pellet. The various components of the compression test system 100 may be supported by a frame 102 to provide stability to the system. A compressive force monitoring system is also provided that includes a force sensor, such as a load cell 142. The compressive force monitoring system is capable of providing a first signal corresponding to the force applied by the ram 108 to a pellet on the platen 140, and is capable of determining the maximum compressive force applied by the ram 108 to the pellet on the platen 140. The compressive force monitoring system may also provide a second signal corresponding to the maximum compressive force applied by the ram 108 to the pellet on the platen 140. The maximum compressive force may be the maximum force applied to the pellet prior to failure or crushing of the pellet.

The compressive test system 100 may be an automated compressive test system controllable by a computer 116 or other programmable control device. The computer 116 may be configured to control the drive motor 118 to move the feed wheel 106 and to control the ram 108 to position a pellet for testing. The computer 116 may receive the first signal corresponding to the force applied by the ram 108 to a pellet on the platen 140 and may receive the second signal corresponding to the maximum compressive force applied by the ram 108 to the pellet on the platen 140. In one alternative, the computer 116 may be adapted to receive the first signal and determine the second signal. The computer 116 may record test parameters and generate reports corresponding to the measured compressive strength of a plurality of pellets tested by the compression test system 100.

The compression test system 100 may also comprise manual controls 114. The manual controls 114 may enable a user to manually operate the compression test system 100. In one embodiment of the system, the manual controls 114 may include controls to turn the system power on or off, controls to advance or reverse the feed wheel 106, controls to raise or lower the hydraulic ram, and controls to turn the hydraulic system on and off. Reversing the feed wheel 106 may be useful to assist in clearing jammed pellets or performing other maintenance on the compression test system. The manual controls 114 may also include one or more settings to enable automated operation of the compression test system 100. Other controls may be provided as desired such that the compression test system 100 may be operated in a manual, semi-automated, or automated manner.

Figure 3A:
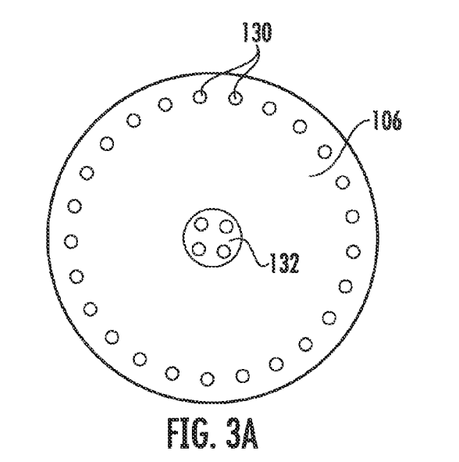
FIGS. 3A-3D are views of a feed wheel for use with a compression test system.

Referring now to FIG. 3A, a top view of a feed wheel 106 for use with a compression test system 100 of the present disclosure is illustrated. As shown the feed wheel 106 may be substantially circular. The feed wheel 106 may have a drive motor attachment portion 132 to enable the feed wheel 106 to be rotated during use of the compression test system. The feed wheel 106 also comprises a plurality of apertures 130 spaced substantially around the circumference of the feed wheel 106, each aperture 130 being adapted to support a pellet. Each aperture 130 may extend through the feed wheel 106 to permit a pellet to pass through the aperture 130 during a compression test. The feed wheel 106 may have a number of apertures 130 corresponding to the number of pellets desired to be tested. In one embodiment of the system, a feed wheel 106 may be provided with one hundred apertures to permit one hundred pellets to be tested. In this manner, a user may load the feed wheel 106 of the compression test system 100 with a desired number of pellets 125 and the compression test system 100 may be capable of operating without further user interaction until the test is complete. In another alternative, the compression test system 100 may be adapted to test an arbitrary number of pellets, including a number of pellets exceeding the number of apertures 130 of the feed wheel 106. For instance, the compression test system 100 may be capable of combining the results from multiple loadings of the feed wheel 106 and reporting the combined test results. In this manner, the compression test system may be utilized to test larger samples of pellets such as 500, 1000, or even more pellets as desired for a given application.

Figure 3B:
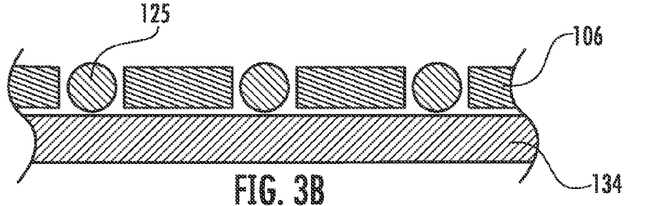
Figure 3C:
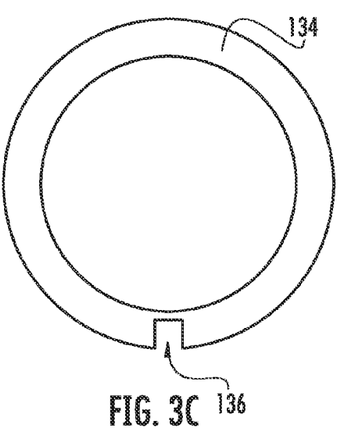

As shown in FIG. 3B, the feed wheel 106 may be positioned above a base plate 134. A plurality of pellets 125 may be provided in the apertures 130 of the feed wheel 106 and the pellets may be supported from below by the base plate 134. In this fashion, the feed wheel 106 and base plate 134 cooperate to form a feed tray adapted to support a plurality of pellets to be tested. As shown in FIG. 3C, the base plate 134 may have a notch 136. The notch 136 may be aligned with the platen 140 and the ram 108 forming the test position where the compressive strength of a pellet 125 is tested.

In one embodiment of the system and method presently disclosed, the feed wheel 106 is engaged by the drive motor 118 such that the feed wheel 106 may be rotated to advance the pellets 125 towards the test position. As will be apparent, when a pellet 125 positioned in an aperture 130 of the feed wheel 106 arrives at the test position, the pellet 125 may pass through the notch 136 of the base plate 134 onto the platen 140. In another embodiment, the platen 140 may extend at least partially into the notch 136 of the base plate 134.

Figure 4A:
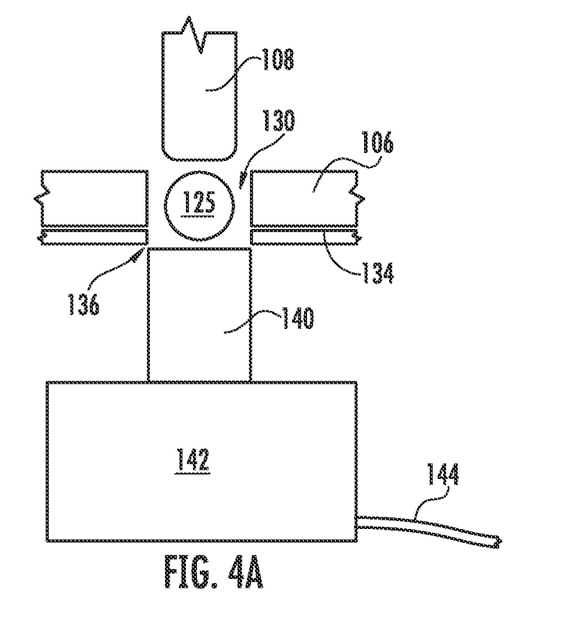
FIGS. 4A-4B are detail views of the compression test system.

The compression test system may be configured for testing the compressive strength of a pellet 125 as shown in FIG. 4A. As illustrated, the feed wheel 106 has been advanced such that the aperture 130 of the feed wheel 106 aligns with the notch 136 of the base plate 134. The notch 136 of the base plate 134 is also aligned with the ram 108 and the platen 140 such that the pellet 125 is positioned between the ram 108 and the platen 140. As illustrated, the platen 140 is connected to a load cell 142. The ram 108 may be lowered into contact with the pellet 125 on the platen 140 to apply compressive force to the pellet 125. As will be apparent, depending upon the size of the pellet 125, the ram 108 may extend into the aperture 130 of the feed wheel 106. The aperture 130 of the feed wheel 106 may therefore be sized to accommodate the ram 108 during testing of the pellet 125.

In the embodiment shown, the platen 140 is connected to a force sensor, such as load cell 142 which produces a first signal 144 corresponding to the force applied by the ram 108 to the pellet 125 on the platen 140. In another embodiment of the system and method, the load cell may be operatively connected to the ram to measure the force applied by the ram to the pellet on the platen. In yet another embodiment, a support structure or other device may be interposed between the platen and the load cell. In yet another embodiment, two or more load cells may be employed, either together or at separate locations.

Figure 5:
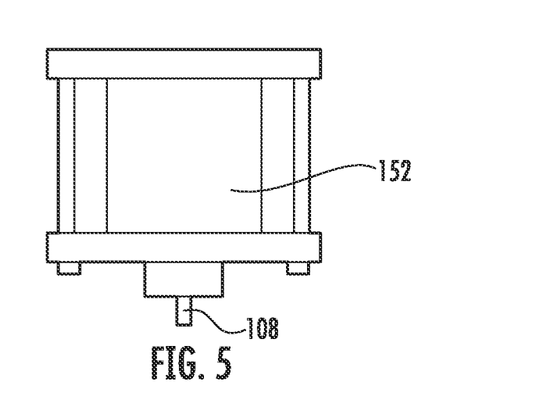
FIG. 5 is a side elevation view of a hydraulic ram assembly for use with a compression test system of the present disclosure.

The ram 108 may be powered by a hydraulic system 152 as illustrated in FIG. 5. A hydraulically powered ram may be capable of applying the compressive force to a pellet in the compression test system presently disclosed. Other types of systems, such as pneumatic systems, may be employed to operate the ram 108 in the compression test system at a range of desired ram speeds. The type of system desired may depend upon the ram speed required, which may be determined by the specifications or requirements of a test process. As an example, ISO 4700 specifies requirements for measuring the compressive load attained to cause breakage of pellets, also referred to as the crushing strength. The specification identifies specific test parameters which must be followed. The compressive test system presently disclosed may be configured to comply with the ISO 4700 parameters. In one embodiment of the system and method for determining the compressive strength of pellets, the speed at which the ram is extended or retracted during a test may be set at 15 millimeters per minute. Other ram speeds are possible, such as between 10 and 20 millimeters per minute, and the ram speed may be adjustable to conform to desired test parameters. In one embodiment, the ram may be extended and retracted at different speeds. For instance, the ram may be extended at between 10 and 20 millimeters per second as desired for the compression test, and may be retracted at a speed greater than 20 millimeters per second to improve the throughput of the compression test system.

During operation the compressive force monitoring system of the compression test system 100 may provide a second signal corresponding to the maximum compressive force applied by the ram 108 to the pellet 125 on the platen 140. The compressive force monitoring system may include a signal processor capable of receiving the first signal and determining the maximum compressive force applied to the pellet on the platen. The signal processor may utilize analog or digital peak detection circuitry. In some embodiments, the signal processor may determine the maximum compressive force by analog peak capture to reduce errors associated with the sampling rate of digital peak detection systems. In one embodiment, a signal processor such as the Daytronic 4077 may be utilized to provide analog peak capture capability.

By way of illustration, as the ram 108 is extended the instantaneous force applied to the pellet 125 and transferred to the load cell 142 increases. The increase may be non-linear and decreases in the measured instantaneous force may occur. The maximum compressive force measured corresponds to the peak. The criteria for determining the maximum compressive force or crushing strength of a pellet may be determined by the specifications or requirements of a given test standard. In one embodiment, when the instantaneous force falls to less than fifty percent (50%) of the peak value, the pellet is considered crushed. In another embodiment, the pellet may be considered crushed when the ram 108 has extended a predetermined distance, such as fifty percent (50%) of the nominal diameter of the pellets being tested. Alternatively, the predetermined distance may be to the midpoint of the aperture 130 of the feed wheel 106. In any case, the greatest force value recorded prior to the pellet being deemed crushed is considered to be the maximum compressive force value.

Figure 3D:
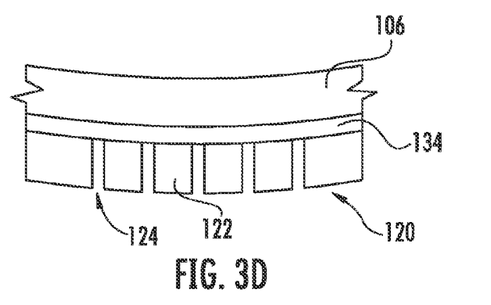

Also disclosed is a compression test system where the moveable feed tray comprises a position indicator having a plurality of position indicating apertures, each position indicating aperture corresponding to a pellet support aperture of the feed tray. As shown in FIG. 3D, a position indicator 120 may be attached to a feed wheel 106. The position indicator 120 may generally be characterized as a ring having a plurality of tabs 122 separated by a plurality of spaces 124 forming the position indicating apertures. The spaces 124 of the position indicator 120 correspond to the pellet supporting apertures 130 of the feed wheel 106.

Figure 6:
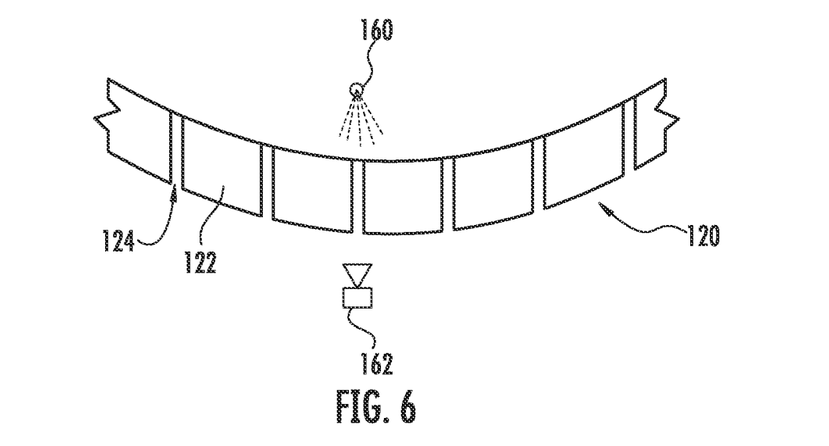
FIG. 6 is a schematic view of an optical position indicator system.

The position indicator 120 may be used to monitor the position of the feed wheel 106. As shown in FIG. 6, a light source 160 may be provided on one side of the position indicator 120 attached to the feed wheel 106, and an optical sensor 162 opposite the light source 160 may be provided on the other side of the feed wheel position indicator 120. In this configuration, the optical sensor 162 receives light from the light sensor 160 passing through the spaces that form the position indicating aperture when the feed wheel is in a desired position. More specifically, when the feed wheel 106 is rotated to align an aperture 130 in the test position such that a pellet 125 may be tested, a space 124 of the position indicator 120 may be aligned between the light source 160 and the optical sensor 162. In this manner, the compression test system 100 is capable of identifying proper positioning of the feed wheel 106 and pellet 125 in the test position when the optical sensor 162 detects the light from the light source 160 passing through the space 124 in the position indicator 120.

Also disclosed is a method for determining the compressive strength of pellets. The method includes providing a feed tray adapted to support a plurality of pellets to be tested, positioning a ram at a first position above a platen to apply a compressive force to a pellet on the platen, advancing the feed tray to position a pellet at a test position between the ram and the platen, detecting the non-arrival of the pellet at the test position, retracting the ram from the first position, advancing the feed tray to position the pellet beneath the ram, and operating the ram to determine the compressive strength of the pellet. As previously noted, the operating speed of the ram may be varied, such as by advancing the ram at a first speed, such as 10 to 20 millimeters per minute, but retracting the ram at a speed greater than 20 millimeters per millimeters per minute, such as retracting at a rate of 100 millimeters per minute or more.

Figure 4B:
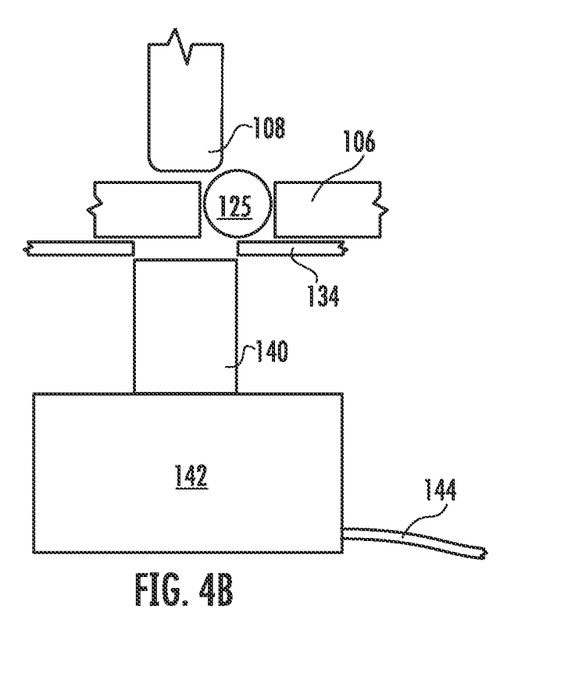

The method presently disclosed may improve the efficiency of compression test systems by reducing the total distance traveled by the ram as compared to prior test systems. Referring generally to FIGS. 1 through 3, a feed tray such as the feed wheel 106 may be provided having a plurality of apertures 130 adapted to support a plurality of pellets to be tested. As shown in FIG. 4A, the ram 108 may be positioned at a first position above the platen 140 and adapted to apply a compressive force to a pellet 125 on the platen 140. The feed wheel 106 may be advanced, such as by the drive motor 118, to position a pellet at a test position between the ram 108 and the platen 140 as previously described. However, as illustrated in FIG. 4B, some pellets 125 may have a diameter that causes the pellet 125 to extend beyond the first position such that the ram 108 in the first position interferes with the advancing pellet 125 resulting in the non-arrival of the pellet 125 at the test position.

The non-arrival of the advancing pellet 125 at the test position may be detected in a variety of ways. In one embodiment, the distance between adjacent pellet supporting apertures 130 of the feed wheel 106 may be correlated to a rotation distance of a drive motor 118. If the drive motor 118 fails to rotate the desired distance, the feed wheel 106 may not have advanced to position a pellet 125 in the test position. In another embodiment, the drive motor 118 may be provided with a torque sensor and, when the torque sensor exceeds a predetermined value, the compression test system 100 may infer that the ram 108 is interfering with a pellet 125 and impeding the advance of the feed wheel 106.

The method of determining the compressive strength of pellets may also include starting the advance of the feed tray and measuring the time the feed tray has been advancing to position a pellet at the test position between the ram 108 and the platen 140, and identifying the non-arrival of the pellet 125 at the test position when the measured time exceeds a predetermined time. In one embodiment of the method, the non-arrival of the advancing pellet 125 at the test position may be detected using a position indicator attached to a feed tray. As previously described, a compression test system 100 may be provided with a position indicator 120. The position indicator 120 may identify the alignment of a feed tray or feed wheel 106 with the test position. During operation of a compression test system and upon completing the test of one pellet 125, a drive motor 118 may be activated to advance the feed wheel 106 to the next position. The time at which the advance of the feed wheel 106 began may be recorded as the "start time". The arrival of the next aperture 130 of the feed wheel 106 at the test position may be identified when an optical sensor 162 detects the light from a light source 160 passing through the next space 124 of the position indicator 120. The non-arrival of a pellet 125 at the test position may therefore be detected if the arrival of the next aperture 130 of the feed wheel 106 is not detected within a predetermined time from the start time. The predetermined time will depend upon the desired speed of the moveable feed tray, such as the rotation speed of a feed wheel 106. The predetermined time may be determined empirically by measuring the time required to advance the feed wheel between adjacent pellet supporting apertures 130.

When the non-arrival of a pellet 125 is detected, the ram 108 is retracted from the first position. The ram 108 may be retracted such that the ram 108 does not interfere with the advancing pellet supported by the feed tray. In one embodiment, the ram 108 may be retracted by a predetermined distance, such as 2 millimeters. The feed tray may then be advanced to position the pellet 125 at the test position. If the pellet 125 continues to interfere with the ram 108, the non-arrival of the pellet 125 at the test position may be detected and the process may be repeated until the ram 108 is sufficiently retracted from the first position such that the ram does not interfere with the pellet 125 supported by the feed tray. Once the feed tray has been advanced to position a pellet 125 beneath the ram 108, the ram 108 may then be operated to determine the compressive strength of the pellet 125 as previously described.

The system and method for testing the compressive strength of pellets may also include data recording, error reporting, and other features to facilitate operation and maintenance of the system. In one embodiment, the compression test system 100 may be capable of recording the first signal and the second signal provided by the compressive force monitoring system. The system may generate reports relating to the maximum compressive strength for one or more tested pellets. The system may also be configured to combined the test results of multiple samples and provide a statistical analysis of the overall test results. In yet another embodiment, the system may be capable of displaying a compressive force profile or force curve for a given pellet throughout a test. The system may also be configured to monitor the deformation of pellets during testing by recording both the force applied to a pellet and the position of the ram during the test. Other reporting and monitoring features may be provided.

The system may also be adapted to generate errors to alert the user to conditions requiring attention. The system may monitor a hydraulic system, drive motor, and system power for proper operation and may generate warnings or alarms should any of these systems cease to function properly. In another embodiment, in the event that the ram is fully retracted by the methods previously described and the feed wheel is still unable to advance a pellet to the test position, an error may be generated and the test discontinued.

The system and method presently disclosed may improve the efficiency of pellet compression test by reducing the distance traveled by the ram as previously described. By way of illustration, a ram travel speed of 15 millimeters per minute and a sample size of 100 pellets are described. Using the system and method presently disclosed, if the ram travel distance is reduced by 3 millimeters for 90% of the pellets in the sample, the overall test time may be reduced by approximately 16 minutes. If the ram travel distance is reduced by 10 millimeters for 90% of the pellets in the sample, the overall test time may be reduced by approximately 53 minutes. As will be apparent, test time is reduced by selecting a first position of the ram to achieve a reduction in ram travel distance, however, test time is increased as the number of pellets interfering with the ram in the first position increases. The compression test system may be further capable of identifying the size of the pellets and adjusting the position of the first position based upon the identified sizes of the pellets in the sample. In this fashion, the compression test system may dynamically respond to variations in pellet size to provide greater efficiency in the test process.

Figure 7:
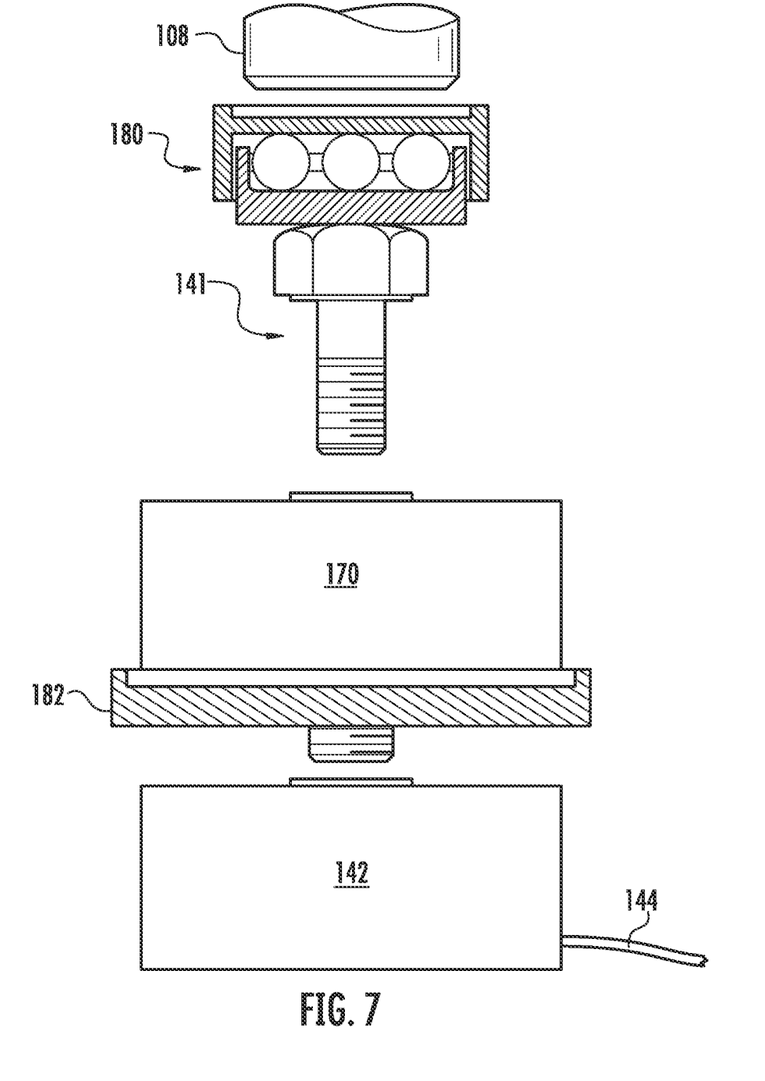
FIG. 7 is a side view of a calibration system for use with a compression test system.

The compression test system presently disclosed may also be calibrated or tested to monitor and maintain the accuracy of the measured compressive forces. As shown in FIG. 7, a second or master load cell 170 may be provided as a calibration standard to determine the accuracy of the load cell 142 of the compression test system. In one embodiment, the platen (not shown) of the compression test system may be removed to provide adequate clearance for insertion of the second load cell 170. As illustrated, an adapter plate 182 having a threaded connector may be attached to the load cell 142 in place of the standard platen. The adapter plate 182 may be configured to support the maser load cell 170. The adapter plate 182 may inhibit lateral movement of the maser load cell 170 and ensure proper alignment of the master load cell 170 with the load cell 142 and the ram 108.

A modified platen or calibration load applicator 141 is provided between the master load cell 170 and the ram 108. The ram 108 may be extended into contact with the calibration load applicator 141, or alternatively, the calibration load applicator 141 may be extended to engage the ram 108. As illustrated, a thrust bearing assembly 180 may be provided between the calibration load applicator 141 and the ram 108 to transfer axial force while facilitating rotation between the calibration load application 141 and the ram 108.

A calibration load or calibration force may be applied to calibrate the compression test system by the ram 108 or the calibration load applicator 141. For example, the ram 108 may be extended as previously described to apply the calibration force. Alternatively, the calibration load applicator 141 may be extended. In one embodiment, the calibration load applicator 141 is a threaded connector, such as a bolt. The threads of the calibration load applicator may engage the master load cell, such that when the calibration load applicator is rotated, the calibration load applicator extends from the master load cell applying an increasing compressive force. In this manner, a calibration force of up to 1,500 pounds or more may be applied.

During the calibration process, the force measured by the master load cell 170 is compared to the force measured by the load cell 142. The difference in forces measured by the master load cell 170 and the load cell 142 may be recorded and applied as calibration factors to subsequent measurements by the load cell 142. If the difference between the measured forces exceed a determined tolerance, the load cell 142 may be removed for repair or replacement as necessary. The load cell 142 may be calibrated through its expected range of operating values to ensure accuracy and linearity. In one embodiment, the load cell 142 may be calibrated from zero to 1200 pounds in 200 pound increments. Other calibrations may also be performed as required for the compression test system, such as verifying the travel speed of the ram or the pressure of the hydraulic system.

While certain embodiments have been described, it will be understood that various changes may be made, equivalents may be substituted, and modifications may be made to adapt a particular situation or material to the teachings of the disclosure without departing from the sprit or scope of the present disclosure.

What is claimed is:

1. A system for determining the compressive strength of pellets comprising:
   a moveable feed tray adapted to support a plurality of pellets to be tested,
   a platen positioned below the moveable feed tray,
   a ram opposite the platen, wherein the ram is configured to apply a compressive force to a pellet on the platen,
   a drive motor engaging the feed tray to position a pellet between the platen and the ram to permit compression testing of the pellet, and
   a compressive force monitoring system including a force sensor, the compressive force monitoring system configured to provide a first signal corresponding to the force applied by the ram to a pellet on the platen and configured to determine the maximum compressive force applied by the ram to the pellet on the platen.

2. The system for determining the compressive strength of pellets as claimed in claim 1, where the ram is hydraulically powered.

3. The system for determining the compressive strength of pellets as claimed in claim 1, where the moveable feed tray is a rotating feed wheel.

4. The system for determining the compressive strength of pellets as claimed in claim 3, where the feed wheel includes a plurality of apertures spaced along the circumference of the feed wheel, each aperture being adapted to support a pellet.

5. The system for determining the compressive strength of pellets as claimed in claim 4, where the feed wheel has at least 100 apertures adapted to support pellets.

6. The system for determining the compressive strength of pellets as claimed in claim 1, where the force sensor comprises a load cell.

7. The system for determining the compressive strength of pellets as claimed in claim 1, where the compressive force monitoring system includes a signal processor for determining the maximum compressive force applied to the pellet on the platen.

8. The system for determining the compressive strength of pellets as claimed in claim 7, where the signal processor determines the maximum compressive force applied to the pellet on the platen by analog peak capture.

9. The system for determining the compressive strength of pellets as claimed in claim 1, where the moveable feed tray further comprises a position indicator.

10. The system for determining the compressive strength of pellets as claimed in claim 9, where the position indicator has a plurality of position indicating apertures, each position indicating aperture corresponding to a pellet support aperture of the feed tray.

11. The system for determining the compressive strength of pellets as claimed in claim 10 further comprising:
    a position detection system configured to detect the position of the feed tray, the position detection system having a light source on one side of the feed tray position indicator and an optical sensor opposite the light source on the other side of the feed tray position indicator, where the optical sensor receives light from the light sensor passing through a position indicating aperture when the feed tray is in a desired position.

12. A method for determining the compressive strength of pellets comprising:
    providing a feed tray adapted to support a plurality of pellets to be tested,
    positioning a ram at a first position above a platen to apply a compressive force to a pellet on the platen,
    advancing the feed tray to position a pellet at a test position between the ram and the platen,
    detecting the non-arrival of the pellet at the test position,
    retracting the ram from the first position,
    advancing the feed tray to position the pellet beneath the ram, and operating the ram to determine the compressive strength of the pellet.

13. The method for determining the compressive strength of pellets as claimed in claim 12, where the step of detecting the non-arrival of a pellet further comprises:
   starting the advance of the feed tray and measuring the time the feed tray has been advancing to position a pellet at the test position between the ram and the platen, and
   identifying the non-arrival of the pellet at the test position when the measured time exceeds a predetermined time.

14. The method for determining the compressive strength of pellets as claimed in claim 12, where the step of advancing the feed tray further comprises advancing the feed tray to position a pellet at a test position between the ram and the platen until the ram in the first position interferes with an advancing pellet supported by the feed tray impeding the advance of the feed tray.

15. The method for determining the compressive strength of pellets as claimed in claim 12, where the step of retracting the ram from the first position comprises retracting the ram from the first position such that the ram does not interfere with the advancing pellet supported by the feed tray.

16. The method for determining the compressive strength of pellets as claimed in claim 12 further comprising:
   retracting the ram from the first position by a predetermined distance,
   advancing the feed tray to position the advancing pellet at the test position,
   detecting the non-arrival of the pellet at the test position, and
   repeating until the ram is sufficiently retracted from the first position such that the ram does not interfere with the pellet supported by the feed tray.

17. A method of calibrating a compression test system comprising
   providing a compression test system having a platen engaging a first load cell and a ram opposite the platen,
   removing the platen of the compression test system,
   providing a second load cell with a known measurement accuracy above the first load cell,
   providing a calibration load applicator and a thrust bearing between the second load cell and the ram, the calibration load applicator being extendable to apply a calibration load to the compression test system, and
   calibrating the first load cell by comparing the force measured by the second load cell with the force measured by the first load cell.

18. The method of calibrating a compression test system of claim 17, where the calibration load applicator is a threaded connector.

19. A calibration system for calibrating a load cell of a compression test system, the calibration system comprising:
   a master load cell positioned above the load cell of the compression test system, and
   a calibration load applicator and a thrust bearing positioned between the master load cell and a ram of the compression test system,
   where the calibration load applicator is extendable to apply a calibration load to the compression test system.

20. A calibration system for calibrating a load cell of a compression test system of claim 19, where the calibration load applicator is a threaded connector.

* * * * *